(12) United States Patent
Dimick

(10) Patent No.: US 6,764,470 B2
(45) Date of Patent: Jul. 20, 2004

(54) EAR PLUG MEDICATION ADMINISTRATION DEVICE

(76) Inventor: Roland P. Dimick, 368 11th Ave., Salt Lake City, UT (US) 84103

( * ) Notice: Subject to any disclaimer, the term of this patent is extended or adjusted under 35 U.S.C. 154(b) by 0 days.

(21) Appl. No.: 10/309,733

(22) Filed: Dec. 3, 2002

(65) Prior Publication Data

US 2003/0105450 A1 Jun. 5, 2003

Related U.S. Application Data

(60) Provisional application No. 60/336,646, filed on Dec. 3, 2001.

(51) Int. Cl.[7] ............................................. A61M 5/178
(52) U.S. Cl. .................... 604/217; 604/93.01; 604/200; 604/257; 606/162
(58) Field of Search .............................. 604/93.01, 257, 604/514, 275, 200, 187, 279, 217, 294, 204, 27, 94.01, 79; 424/437, 434; 606/234–236, 109, 162; 222/541.3, 541.6, 92, 94, 541.9

(56) References Cited

U.S. PATENT DOCUMENTS

| 2,737,953 A | | 3/1956 | Wiltein |
| 3,625,213 A | | 12/1971 | Brown |
| 3,777,949 A | * | 12/1973 | Chiquiari-Arias ........ 222/541.8 |
| 4,258,714 A | * | 3/1981 | Leopoldi et al. ............ 604/118 |
| 4,752,288 A | * | 6/1988 | Hussey ........................ 604/111 |
| 4,781,714 A | | 11/1988 | Eckenhoff et al. |
| 4,995,867 A | | 2/1991 | Zollinger |
| 5,176,654 A | | 1/1993 | Schreiber |
| 5,512,047 A | | 4/1996 | Dvorak |
| 5,674,196 A | | 10/1997 | Donaldson et al. |
| 5,772,685 A | * | 6/1998 | Crowe et al. ............... 606/236 |
| 5,851,199 A | | 12/1998 | Peerless et al. |
| 6,120,484 A | | 9/2000 | Silverstein |
| 6,341,718 B1 | * | 1/2002 | Schilthuizen et al. ....... 222/207 |
| 6,357,626 B1 | * | 3/2002 | Zhang et al. ................. 222/78 |
| 6,379,342 B1 | * | 4/2002 | Levinson .................... 604/310 |
| RE37,734 E | * | 6/2002 | Buehler ...................... 222/209 |
| 6,432,117 B1 | * | 8/2002 | Murray ...................... 606/162 |
| 6,540,718 B1 | * | 4/2003 | Wennek ................... 604/94.01 |
| 6,547,808 B2 | * | 4/2003 | Tuckey et al. .............. 606/234 |
| 6,666,359 B2 | * | 12/2003 | Lau et al. ................. 222/541.5 |

FOREIGN PATENT DOCUMENTS

EP          0 319 501 A2  *  7/1989

* cited by examiner

Primary Examiner—Brian L. Casler
Assistant Examiner—Cris L. Rodriguez
(74) Attorney, Agent, or Firm—Clayton, Howarth & Cannon, P.C.

(57) ABSTRACT

A device for delivering a beneficial agent within a body cavity such as the ear canal. The device preferably includes a soft resilient casing that can be compressed to fit at least partially within the ear canal. Once inserted in the ear canal, the casing expands to form a seal between a boundary defining the ear canal and the device. The soft casing preferably encapsulates the beneficial agent within a reservoir formed inside the soft casing. As the device is squeezed, the beneficial agent is ejected through a release point. The device then maintains the beneficial agent within the ear canal until the beneficial agent has had time to take effect.

37 Claims, 1 Drawing Sheet

EAR PLUG MEDICATION ADMINISTRATION DEVICE

CROSS-REFERENCE TO RELATED APPLICATIONS

This application claims the benefit of U.S. Provisional Application No. 60/336,646, filed Dec. 3, 2001, now abandoned which is hereby incorporated by reference herein in its entirety, including but not limited to those portions that specifically appear hereinafter.

STATEMENT REGARDING FEDERALLY SPONSORED RESEARCH OR DEVELOPMENT

Not Applicable.

BACKGROUND OF THE INVENTION

1. The Field of the Invention.

The present invention relates generally to devices for delivering beneficial agents into body cavities, and more particularly, but not necessarily entirely, to devices for delivering medical agents into the ear canal.

2. Description of Related Art.

It is common practice to place medication into the ear canal of patients suffering from ear aches or infections. For example, children are often afflicted with otitis, or inflamation of the ear, which may be treated by placing medication into the ear canal. A common procedure for placing medication in the ear canal of children involves placing the medication into the ear canal using a dropper. Cotton is commonly placed in the child's ear to help maintain the medication in place, since movement of the child may cause the medication to become displaced before it has a chance to take effect.

A drawback of this method is that since cotton is absorbent, it tends to absorb the medication and does not create a seal to maintain the medicine within the ear canal. To help remedy this problem, it is known to wet the cotton with a fluid such as water or the medication prior to inserting it into the ear canal. The wetted cotton is then less able to absorb the medication. However, placing fluid on the cotton is inconvenient and may tend to spread the fluid onto the child or surrounding area.

Attempts have been made in the prior art to provide alternate devices to assist in administering medication to the ear canal. For example, U.S. Pat. No. 2,737,953 (granted Mar. 13, 1956, to Wiltein) discloses a funnel shaped device having a pair of openings. The device is inserted into the ear canal and the medication is applied through one of the openings. The other opening serves as an air vent so that the medication can flow into the ear canal. The funnel shaped device is configured to create a plug to maintain the medication within the ear canal once it has been administered. The openings are required to be small so that the device can fit within the ear canal, and so that the openings prohibit the medication from flowing back out of the ear canal. However, it may be difficult to administer the medication through the opening due to the viscosity of the medication and the small size of the opening. Furthermore, since the medication is applied to the exterior of the device, the medication is likely to be spread if the user contacts the external portion of the device after the medication has been applied. Moreover, since the medication and the funnel device are separate elements that must be handled, administration of the medication is more cumbersome.

Another device for introducing medication into the ear canal is disclosed in U.S. Pat. No. 5,674,196 (granted Oct. 7, 1997, to Donaldson et al.) This device includes an ear plug having a pair of conduits. A syringe is attached to one of the conduits to inject medication into the ear canal, and the other conduit serves as an air vent. A drawback of this device is that it requires the use of a syringe, which may not be available in some situations. Furthermore, the need for a syringe increases the cost and complexity of administering the medication.

The prior art is thus characterized by several disadvantages that are addressed by the present invention. The present invention minimizes, and in some aspects eliminates, the above-mentioned failures, and other problems, by utilizing the methods and structural features described herein.

BRIEF SUMMARY OF THE INVENTION

It is therefore an advantage of the present invention to provide an ear plug medication administration device that is simple in design, manufacture, and use.

It is another advantage of the present invention to provide such an ear plug medication administration device that maintains the medication within the patient's ear canal.

It is a further advantage of the present invention, in accordance with one aspect thereof, to provide an ear plug medication administration device that includes the medication within the device.

It is an additional advantage of the invention, in accordance with one aspect thereof, to provide an ear plug medication administration device that prevents the spread of the medication and other fluids.

The above advantages and others not specifically recited are realized in a specific illustrative embodiment of an ear plug medication administration device. The device preferably includes a soft resilient casing which can be compressed to fit at least partially within the ear canal. Once inserted in the ear canal, the casing expands to form a seal between the ear canal and the device. The soft casing preferably encapsulates the beneficial agent within a reservoir formed inside the soft casing. The device may include an impervious liner between the soft casing and the beneficial agent. As the device is squeezed, the beneficial agent is ejected through a release point. The device then retains the beneficial agent within the ear canal until the beneficial agent has had time to take effect. A cord may be attached to the device to facilitate removal from the ear canal.

Additional advantages of the invention will be set forth in the description that follows, and in part will be apparent from the description, or may be learned by the practice of the invention without undue experimentation. The advantages of the invention may be realized and obtained by means of the instruments and combinations particularly pointed out in the appended claims.

BRIEF DESCRIPTION OF THE DRAWINGS

The above features and advantages of the invention will become apparent from a consideration of the subsequent detailed description presented in connection with the accompanying drawings in which.

DETAILED DESCRIPTION OF THE INVENTION

Figure 1:
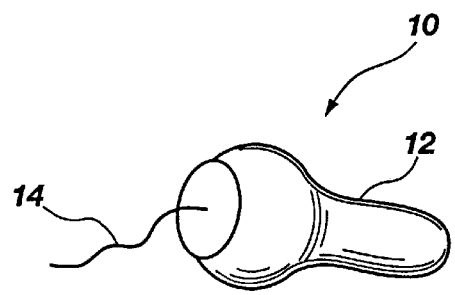
FIG. 1 is a perspective view of an ear plug medication administration device in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Referring now to FIG. 1, there is shown is a perspective view of an ear plug medication administration device, designated generally at 10, in accordance with the principles of the present invention. The ear plug medication administration device 10 shown in FIG. 1 is configured in size and shape to fit within a body cavity such as the ear canal. However, it will be appreciated that the device 10 may be sized and shaped in various different configurations within the scope of the present invention for use in the ear canal and other body cavities, such as the nostrils for example.

The device 10 may include a casing 12, which is preferably formed of a soft resilient material, such as foam rubber for example. It will be appreciated that other materials may be used to form the casing 12 within the scope of the present invention. The material forming the casing 12 is preferably compressible and has an elastic memory such that when a compressive force is applied to the casing 12, the volume of the casing 12 is reduced so that the casing 12 can fit within a body cavity. After the compressive force is removed, the casing 12 preferably expands such that the volume is increased to substantially its original condition. This allows the casing 12 to form a seal within the body cavity.

A handle or safety cord 14, may be attached to an end of the device 10 for facilitating grasping of the device 10 to extract the device 10 from the body cavity. The safety cord 14 is illustrated as a flexible strand. However, it will be appreciated that the safety cord 14 may be configured as a tab or flange, for example, and may be formed as an integral part of the casing 12.

Figure 2:
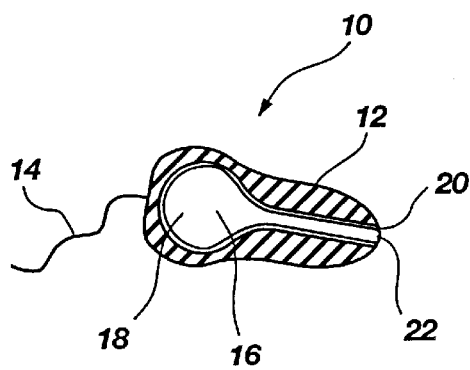
FIG. 2 is a side, cross-sectional view of an ear plug medication administration device of FIG. 1.
Figure 3:
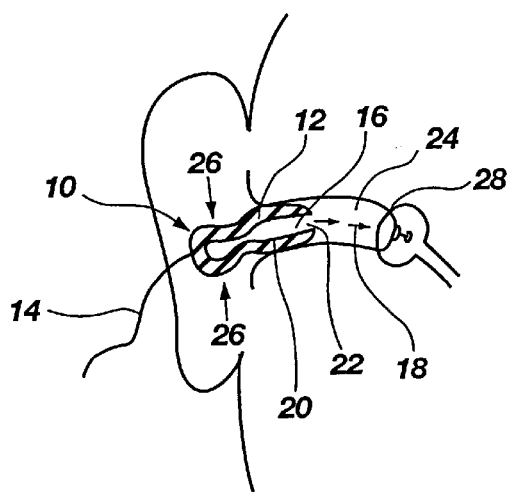
FIG. 3 is a side, break-away cross-sectional view of an ear plug medication administration device being inserted in a patient's ear canal.

As shown in FIG. 2, which presents a side, cross-sectional view of an ear plug medication administration device 10, the casing 12 preferably encapsulates a reservoir 16 wherein a beneficial agent 18 may be contained. The reservoir 16 may be sized to contain a single dose of the beneficial agent 18. The beneficial agent 18 may include any variety of substances desired to be administered within the body cavity for a variety of different types of treatments. For example, the beneficial agent 18 may include medications such as antipyrine/benzocaine liquid for the treatment of otitis. Similarly, other examples of conditions and beneficial agents 18 in which the device 10 may be beneficial include: 1) otitis externa, an infection of the external ear canal in which antibiotic and/or anti-inflammatory medication would be administered to eradicate the infection and/or reduce discomfort; 2) otitis media without perforation, an infection of the middle ear space, in which an anesthetic medication would be administered to relieve pain; and 3) otitis media with perforation (such as with pressure equalization tubes) in which antibiotic medication would be administered to eradicate the infection behind the tympanic membrane 28 (as shown in FIG. 3). It will be appreciated, however, that the beneficial agent 18 may include any of a variety of suitable substances for treatment of various conditions, within the scope of the present invention.

The reservoir 16 may be lined with an impermeable liner 20 to contain the beneficial agent 18 within the reservoir 16, and keep it from migrating into the casing 12. "Impermeable" as referred to herein is defined as a characteristic of preventing the flow of a fluid. Thus, the impermeable liner 20 may be formed of any suitable material that is substantially impervious to the beneficial agent 18, such as a plastic material for example.

A release point 22 is preferably formed in an end of the device 10. The release point 22 is the location where the beneficial agent 18 is ejected from the device 10. The release point 22 may be formed as an exposed portion of the liner 20, a thin or weakened portion of the casing 12, or a type of plug sealing the reservoir 16, for example. The material at the release point 22 is formed such that when the device 10 is compressed, the increased pressure of the beneficial agent causes the reservoir 16 to be ruptured at the release point 22 so the beneficial agent may be ejected at the release point 22.

Use of the device 10 is now explained with reference to FIG. 3 which shows a side, break-away cross-sectional view of an ear plug medication administration device 10 being inserted in a patient's ear canal 24. The device 10 is squeezed, as indicated by the reference numerals 26, to compress the soft casing 12 so that the device can fit within the ear canal 24. As the device 10 is squeezed, the pressure on the beneficial agent 18 increases and forces the release point 22 to be opened. The beneficial agent 18 is then ejected into the ear canal 24 for treatment of the tympanic membrane 28, or the middle ear space behind the tympanic membrane 28, or the ear canal 24 itself. Once inserted, the casing 12 expands to form a seal between the device 10 and the ear canal 24 so that the beneficial agent 18 is maintained within the ear canal 24. After sufficient time has passed to allow the beneficial agent 18 to take effect, the device 10 may be removed by grasping the safety cord 14 and pulling the device 10 from the ear canal 24.

Figure 4:
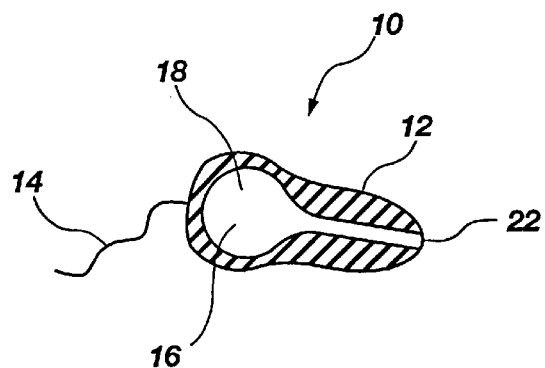
FIG. 4 is a side, cross-sectional view of an alternative embodiment ear plug medication administration device.

Reference will now to made to FIG. 4 to describe a second embodiment of the present invention. As previously discussed, the presently preferred embodiments of the invention illustrated herein are merely exemplary of the possible embodiments of the invention, including that illustrated in FIG. 4.

It will be appreciated that the second embodiment of the invention illustrated in FIG. 4 contains many of the same structures represented in FIGS. 1–3 and only the new or different structures will be explained to most succinctly explain the additional advantages which come with the embodiments of the invention illustrated in FIG. 4.

FIG. 4 shows a side, cross-sectional view of an alternative embodiment ear plug medication administration device 10 which is similar to that of FIG. 2 except that the casing 12 is impermeable to the beneficial agent 18, thus eliminating the need for the liner 20.

In view of the foregoing description, those skilled in the art of forming products of foam-like materials will understand how to make the device in accordance with the principles of the present invention.

In accordance with the features and combinations described above, a preferred method of administering a beneficial agent to a patient's ear canal includes the steps of:

(a) obtaining a device containing said beneficial agent therein;

(b) squeezing said device to cause said device to compress and eject said beneficial agent into said ear canal;

(c) inserting said device into said ear canal;

(d) allowing said device to expand to seal said ear canal to maintain said beneficial agent within said ear canal;

(e) leaving said device within said ear canal for a period of time to allow said beneficial agent to take effect; and (f) pulling on a handle attached to said device to remove said device from said ear canal.

In view of the foregoing, it will be appreciated that the present invention provides an ear plug medication administration device which is simple in design, manufacture, and use, and which contains the medication within the device. The present invention also provides an ear plug medication administration device that maintains the medication within the patient's ear canal and prevents the spread of the medication and other fluids.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiments of the invention, it will be apparent to those of ordinary skill in the art that numerous modifications, including, but not limited to, variations in size, materials, shape, form, function, and manner of operation, assembly, and use may be made without departing from the principles and concepts set forth herein.

What is claimed is:

1. A device for introducing a beneficial agent into a body cavity of a recipient, said device comprising:

a resilient casing configured to be compressed to fit at least partially within said body cavity of said recipient, said resilient casing further being configured to expand after being compressed to conform to said body cavity and to form a seal within said body cavity, said resilient casing comprising an impermeable barrier defining an enclosed reservoir for containing said beneficial agent;

wherein said device is configured to eject said beneficial agent upon being compressed to deliver said beneficial agent to said body cavity, and wherein said device is further configured to maintain said beneficial agent within said body cavity.

2. The device of claim 1, further comprising a handle for grasping the device.

3. The device of claim 2, wherein said handle comprises a cord.

4. The device of claim 1, wherein said resilient casing further comprises a release point defining a location where said beneficial agent is ejected from said device.

5. The device of claim 4, wherein said release point is defined by a weakened portion of said resilient casing.

6. The device of claim 1, wherein said resilient casing comprises an inner impermeable layer and an exterior layer.

7. The device of claim 6, wherein said exterior layer comprises a compressible material having an elastic memory such that when a compressive force is applied to said compressible material, a volume of said compressible material is reduced, and after said compressive force is removed, said compressible material expands such that said volume is increased.

8. The device of claim 7, wherein said compressible material is a foam material.

9. The device of claim 1, wherein said resilient casing comprises a small dimensioned portion configured to be inserted within said body cavity, and a large dimensioned portion configured to define a majority of a volume of the reservoir.

10. A device for introducing a beneficial agent into a body cavity of a recipient, said device comprising:

a casing formed of a compressible material having an elastic memory such that when a compressive force is applied to said compressible material, a volume of said compressible material is reduced, and after said compressive force is removed, said compressible material expands such that said volume is increased, said casing defining an enclosed reservoir for containing said beneficial agent;

wherein said device is configured to be compressed to expel said beneficial agent into said body cavity and said device is further configured to expand after being compressed to seal said beneficial agent within said body cavity.

11. The device of claim 10, further comprising a handle for grasping the device.

12. The device of claim 11, wherein said handle comprises a cord.

13. The device of claim 10, wherein said casing further comprises a release point defining a location where said beneficial agent is ejected from said device.

14. The device of claim 13, wherein said release point is defined by a weakened portion of said casing.

15. The device of claim 10, wherein said casing comprises an inner impermeable layer and an exterior layer.

16. The device of claim 10, wherein said compressible material is a foam material.

17. The device of claim 10, wherein said casing comprises a small dimensioned portion configured to be inserted within said body cavity, and a large dimensioned portion configured to define a majority of a volume of the reservoir.

18. A device for introducing a beneficial agent into a body cavity of a recipient, said device comprising:

a casing configured to be compressed to fit at least partially within said body cavity of said recipient, said casing comprising a compressible layer and an impermeable layer, said impermeable layer defining an enclosed reservoir for containing said beneficial agent;

wherein said device is configured to expel said beneficial agent upon being compressed to deliver said beneficial agent to said body cavity, and wherein said device is further configured to maintain said beneficial agent within said body cavity.

19. The device of claim 18, further comprising a handle for grasping the device.

20. The device of claim 19, wherein said handle comprises a cord.

21. The device of claim 18, wherein said casing further comprises a release point defining a location where said beneficial agent is ejected from said device.

22. The device of claim 21, wherein said release point is defined by a weakened portion of said casing.

23. The device of claim 18, wherein said compressible layer comprises a compressible material having an elastic memory such that when a compressive force is applied to said compressible material, a volume of said compressible material is reduced, and after said compressive force is removed, said compressible material expands such that said volume is increased.

24. The device of claim 23, wherein said compressible material is a foam material.

25. The device of claim 18, wherein said impermeable layer is a plastic layer.

26. A system for providing treatment within a body cavity of a patient, said system comprising:
- a device having a casing, said casing being formed of a compressible material having an elastic memory such that when a compressive force is applied to said compressible material, a volume of said compressible material is reduced, and after said compressive force is removed, said compressible material expands such that said volume is increased, said device further comprising a reservoir within said casing; and
- a beneficial agent contained in said reservoir for providing treatment to said patient;
- wherein when said resilient casing is compressed, said beneficial agent is expelled from said reservoir for providing treatment within said body cavity, and said resilient casing thereafter expands to conform to said body cavity to maintain said beneficial agent within said body cavity.

27. The system of claim 26, wherein said compressible material is a foam material.

28. The system of claim 26, wherein said beneficial agent comprises a medication.

29. The system of claim 28, wherein said beneficial agent comprises an antibiotic medication.

30. The system of claim 28, wherein said beneficial agent comprises an anti-inflammatory medication.

31. The system of claim 28, wherein said beneficial agent comprises an anesthetic medication.

32. The system of claim 26, wherein said device further comprises a handle for grasping the device.

33. The system of claim 32, wherein said handle comprises a cord.

34. The system of claim 26, wherein said device further comprises an impermeable layer enclosing said reservoir.

35. The system of claim 26, wherein said device further comprises a release point defining a location where said beneficial agent is expelled from said device.

36. The system of claim 26, wherein said device comprises a first portion configured to define a majority of a volume of the reservoir and a second portion configured to be inserted within said body cavity, said first portion having a larger dimension than said second portion.

37. A device for introducing a beneficial agent into an ear canal of a recipient, said device comprising:
- a resilient casing comprised of a compressible material having an elastic memory such that when a compressive force is applied to said compressible material, a volume of said compressible material is reduced, and after said compressive force is removed, said compressible material expands such that said volume is increased, said resilient casing being configured to fit at least partially within said ear canal of said recipient, said resilient casing being further configured to conform to said ear canal to form a seal between a boundary defining said ear canal and said resilient casing, said resilient casing further comprising an impermeable barrier;
- a reservoir for containing said beneficial agent, said reservoir being enclosed by said impermeable barrier;
- a release point formed as a weakening in said resilient casing to define a location where said beneficial agent is expelled from said reservoir; and
- a handle for grasping said device to remove said device from said ear canal, said handle comprising a cord;
- wherein said device is configured to expel said beneficial agent upon being compressed to deliver said beneficial agent to said ear canal, and wherein said device is further configured to maintain said beneficial agent within said ear canal.

* * * * *